United States Patent [19]
Beaty et al.

[11] Patent Number: 5,692,904
[45] Date of Patent: Dec. 2, 1997

[54] METHOD AND MEANS FOR AFFIXING A COMPONENT TO A DENTAL IMPLANT

[75] Inventors: Keith D. Beaty; Thomas S. Heylmum, both of West Palm Beach, Fla.

[73] Assignee: Implant Innovations, Inc., West Palm Beach, Fla.

[21] Appl. No.: 401,342

[22] Filed: Mar. 9, 1995

Related U.S. Application Data

[63] Continuation-in-part of Ser. No. 208,212, Mar. 10, 1994, Pat. No. 5,437,550, which is a continuation-in-part of Ser. No. 16,538, Feb. 11, 1993, Pat. No. 5,322,443.

[51] Int. Cl.[6] ............................................. A61C 3/00
[52] U.S. Cl. ........................... 433/141; 433/173; 81/451
[58] Field of Search ............................ 433/141, 173, 433/174; 81/451

[56] References Cited

U.S. PATENT DOCUMENTS

| | | | |
|---|---|---|---|
| 2,276,470 | 3/1942 | Dodelin | 81/451 |
| 4,072,070 | 2/1978 | Finn | 81/451 |
| 5,026,285 | 6/1991 | Durr et al. | 433/141 |
| 5,062,800 | 11/1991 | Niznick | 433/173 |
| 5,064,375 | 11/1991 | Jorneus | 433/174 |
| 5,105,690 | 4/1992 | Lazzara et al. | |
| 5,120,221 | 6/1992 | Orenstein et al. | |
| 5,145,371 | 9/1992 | Jorneus | 433/174 |
| 5,437,550 | 8/1995 | Beaty et al. | 433/173 |
| 5,462,436 | 10/1995 | Beaty et al. | 433/173 |

*Primary Examiner*—Cary E. O'Connor
*Attorney, Agent, or Firm*—Arnold, White & Durkee

[57] ABSTRACT

A tool for affixing a component to a dental implant fixture with a screw passing through the component and threaded into the implant fixture, in which the tool has two parts telescopically interfitting one within the other, the outer part being tubular for carrying the component at one end, and the inner part fitted at one end for carrying the screw positioned within the component, whereby the component and the screw within it can be carried together to the implant fixture where the outer part is used to hold the component in place while the inner part is used to drive the screw relative to the implant fixture.

13 Claims, 9 Drawing Sheets

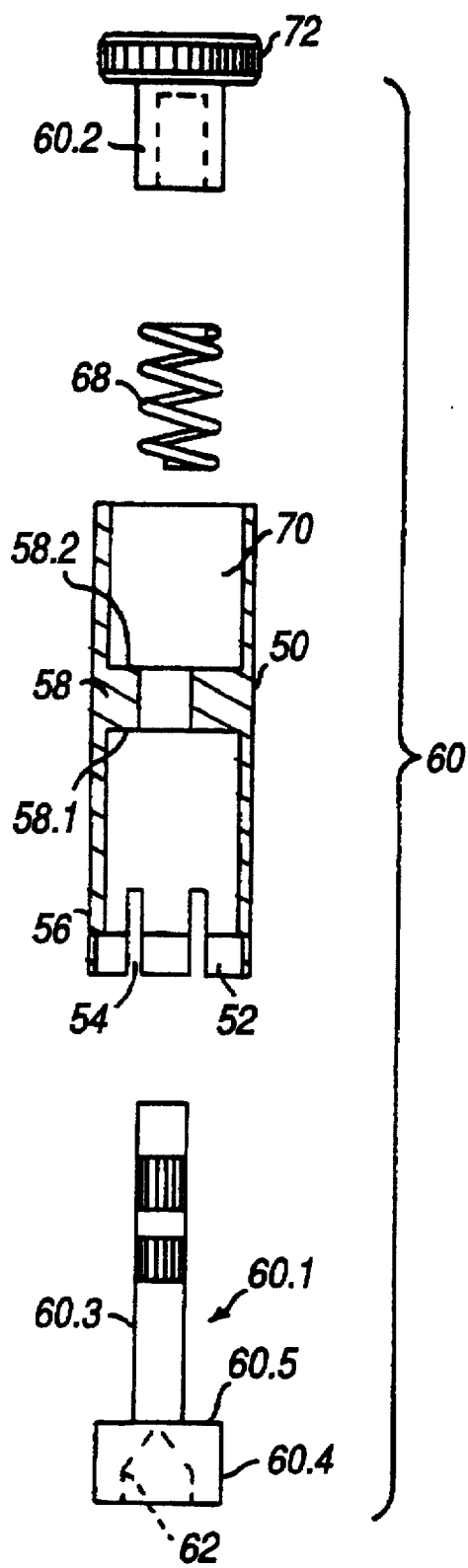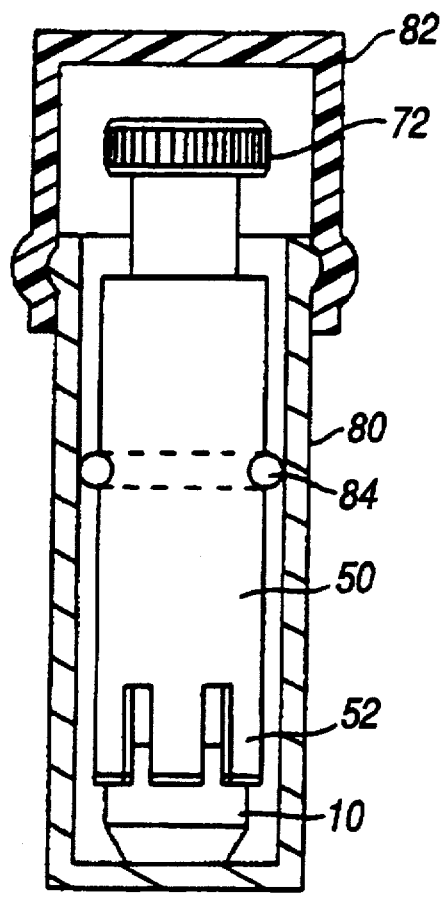
FIG. 8
FIG. 9

METHOD AND MEANS FOR AFFIXING A COMPONENT TO A DENTAL IMPLANT

This application is a continuation-in-part of U.S. patent application Ser. No. 08/208,212, filed on Mar. 10, 1994, now U.S. Pat. No. 5,437,550, which in turn is a continuation-in-part of U.S. patent application Ser. No. 08/016,538 filed on Feb. 11, 1993, now issued as U.S. Pat. No. 5,322,443.

FIELD OF THE INVENTION

This invention relates to the art of restorative dentistry, and more particularly to that segment of the art which employs artificial roots to restore edentulous patients.

BACKGROUND OF THE INVENTION

At the present time, owing in part to its predictable success, the endosseous dental implant fixture in cylindrical form is the artificial root most frequently chosen for restoring dentition to edentulous patients when implant treatment is selected. These and other forms of artificial tooth roots are conveniently designed to receive and retain, sometimes removably, a variety of intermediate components including abutments which prosthodontists use to support artificial dentition on artificial roots. The intermediate components are necessarily small parts which must be manipulated into sometimes deep posterior locations in the patient's mouth and there assembled on an existing implant fixture or fixtures into rigid and reliable structures which can withstand the forces of mastication. More and more commonly the implant fixtures have internally threaded bores for receiving small screws which are used to attach the intermediate components to the implant fixtures, and to each other, and they have hexagonal or other non-circular means for anti-rotationally engaging such intermediate components. For biological reasons the implant fixtures and intermediate components are most often made of titanium and its dilute alloys, while the screws are made of the same metals or of gold, for example. Typical diameters of implant fixtures are from about 3 min. to about 5 min. Typical screw diameters are about 2 mm. or less. Typically, intermediate components have diameters in the same range as implant fixtures, and lengths short enough to be encompassed within an artificial tooth, or shorter. The problems of carrying such components to an implant fixture installed in a patient's jawbone and there affixing a component to the implant with a screw, and rotating the components to engage or mate with anti-rotational features on the implant fixture, without cross-threading the screw in the threaded bore of the implant fixture, are obvious.

Abutments and other intermediate components are made in a wide variety; some are small transmucosal components as small as one millimeter long, while some are several millimeters long intended to form the core of an artificial tooth; others may extend on an axis different from the longitudinal axis of the implant fixture, for adjusting the alignment of an artificial tooth relative to its neighbors; all must be affixed to the implant fixture. To do this the dental professional must hold the component in place on the implant fixture while inserting a screw through a small hole in the component and turning the screw in the threaded bore of the implant fixture until the screw is tight and the component is firmly affixed to it. This task becomes particularly onerous when the implant fixture is installed in a posterior region in the patient's mouth.

A dental clamp for gripping a cylindrical abutment is shown in U.S. Pat. No. 5,120,221 dated Jun. 9, 1992.

SUMMARY OF THE INVENTION

In accordance with the present invention, there is provided a tool for use in manually positioning and manipulating a selected article at a prepared implant site in a bone in the mouth of a patient. The tool comprises an article holder having a lower end for engaging the top of the selected article; a fastener passing longitudinally through the article holder for cooperation with the selected article engaged by the lower end of the article holder; a driver mounted for rotation in the article holder and extending downwardly through the article holder for engaging the top of the fastener, so that the fastener can be rotated by rotating the driver, the top of the driver extending above the top of the article holder so that the driver can be turned with the fingers of the person positioning and manipulating the selected article; and a handle attached to the top of the article holder and extending upwardly from the article holder to permit the person positioning and manipulating the selected article to simultaneously position and manipulate the holder and turn the driver with fingers of the same hand.

In one embodiment of the invention, the selected article is an implant carrier, and the fastener is a screw for attaching an implant to the implant carrier. In another embodiment, the selected article is an implant abutment, and the fastener is a screw for attaching the abutment to an implant.

In the preferred form of the present invention for handling abutments or other intermediate components, the tool employs two telescopically-interfitting parts, the inner one removably attached to the screw head and the other removably attached to a supraginvival end of the intermediate component, for holding the screw and the component in relative positions suitable for installing them on the implant fixture and carrying them to the implant fixture in those positions, and there while holding the component in place on the implant fixture with the outer part using the inner part to turn the screw into the threaded bore of the implant fixture. Cross-threading of the screw is prevented by virtue of the fact that the component is firmly seated on the implant fixture with the aid of the outer part and the two telescopically interfitting parts align the screw accurately with relation to the threaded bore. The two interfitting parts can be designed to form an assembly including resilient means, such as a spring, to enable the inner part to press down on the outer part while turning the inner part, so that the entire installation procedure can be completed with two fingers (e.g.: thumb and forefinger) while turning the inner part to install the screw. When the installation procedure is finished both parts can be detached from the screw and the component simply by pulling them away in the supragingival direction. It is not necessary to tighten the screw to its final torque limit with the carrying and affixing means of the present invention; that task can be performed with a separate torque-limited driver.

The invention lends itself to packaging in a sealed container, which may be a sterile container if desired, so that a component and related screw may be delivered to a dental professional in a "ready for installation" condition. Thus, the present invention simplifies an onerous task while improving the accuracy with which that task is done, and saves the user valuable time while reducing the risk of infection.

In the preferred form of the invention for use in handling an implant carrier to manually insert a dental implant into a prepared implant site in a bone in the mouth of a patient, the tool comprises a holder for the implant carrier, the holder having a lower end for engaging the top of the implant carrier so that the implant carrier is retained in the holder; a driver mounted for rotation in the holder and extending downwardly through the holder for engaging the top of the screw, so that the screw can be rotated by rotating the driver, the top of the driver extending above the top of the holder so that the driver can be turned with the fingers of the person installing the implant; and a handle attached to the top of the holder and extending upwardly from the holder to permit the person installing the implant to simultaneously manipulate the holder and turn the driver with fingers of the same hand. Mating male and female anti-rotation elements are formed on the top of said implant and the bottom of said implant carrier, and the bottom of the holder forms a socket for receiving the top of the implant carrier. The handle is formed as an integral part of said holder, and extends over the top of the driver. The top of the driver forms an enlarged head which extends laterally beyond the handle to facilitate turning of the driver with the same fingers that grip the handle.

BRIEF DESCRIPTION OF THE DRAWINGS

The appended drawings illustrate the background of the invention and exemplary embodiments of it. In these drawings:

FIG. 8 is an exploded view of the parts of the embodiment shown in FIGS. 6 and 7;

FIG. 9 is a longitudinal view partly in sections showing the embodiment of FIG. 6 in a sealed container;

DETAILED DESCRIPTION OF THE PREFERRED EMBODIMENTS

Figure 1B:
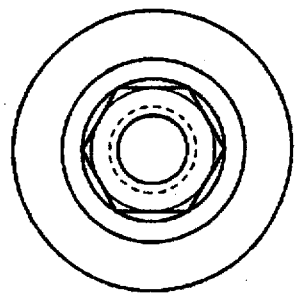
FIGS. 1A and 1B are end views of FIG. 1.
Figure 1:
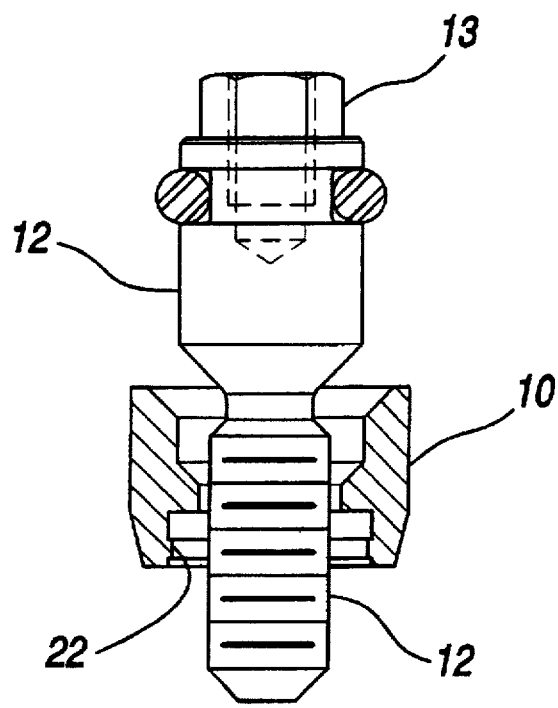
FIGS. 1 and 2 illustrate, respectively, a transmucosal component and related screw and a dental implant fixture on which they are to be installed.
Figure 1A:
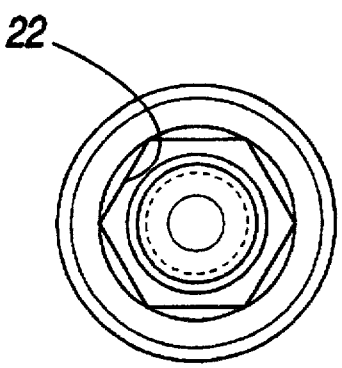
Figure 2:
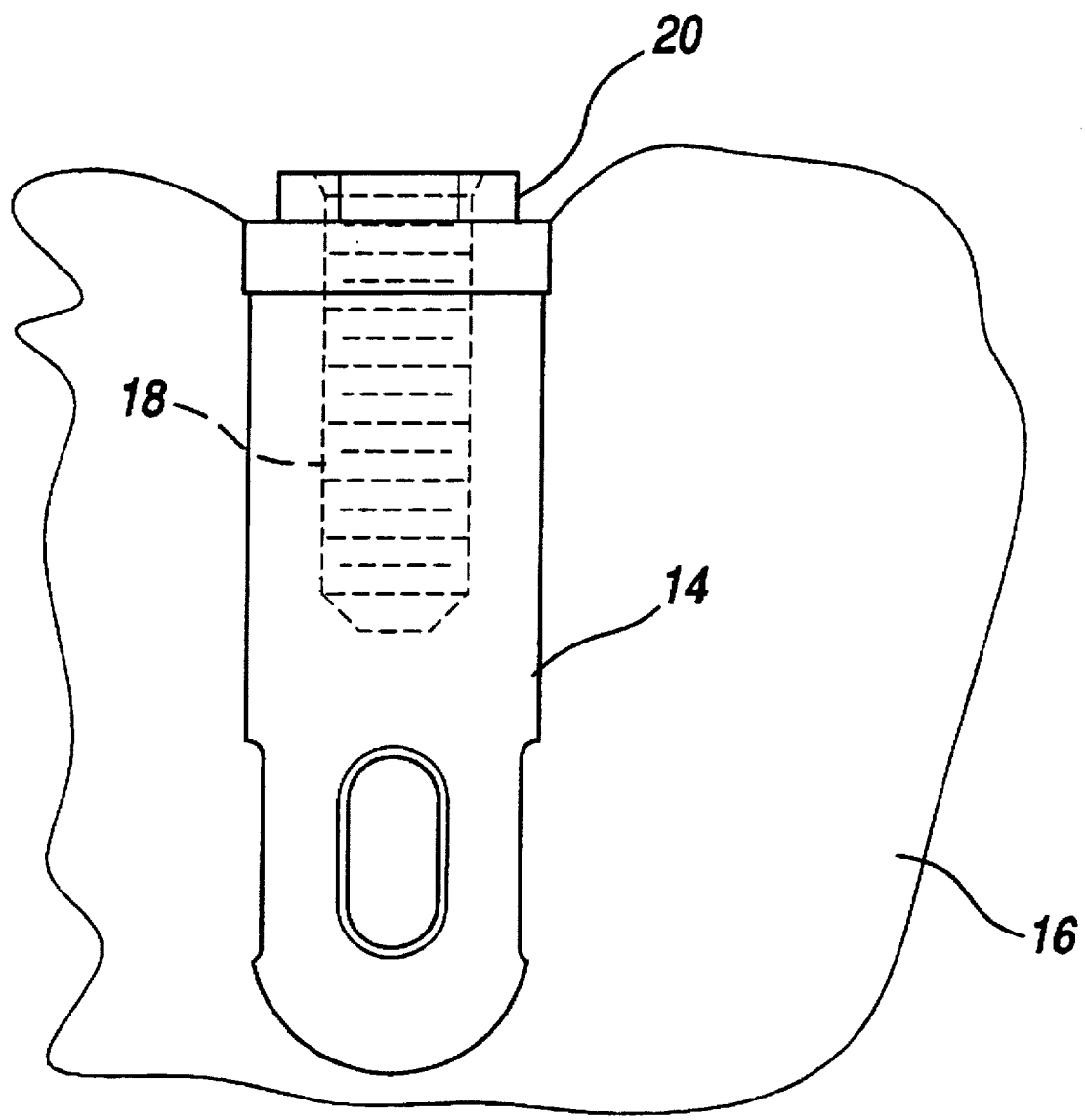

FIGS. 1 and 2 show a typical transmucosal component 10 and a typical screw 12 for use to install the transmucosal component on a dental implant fixture 14 which has been installed in jawbone 16. The screw and the transmucosal component are shown in relative positions suitable for installing them on the implant fixture, which has an internally-threaded bore 18 for receiving the screw. As is typical in the art, the implant fixture may have an anti-rotation boss 20 extending supragingivally from it, and the transmucosal component 10 may have a mating socket 22 for interfitting with the boss 20. In practice, the boss and the socket may be reversed. In either case, the transmucosal component must be fitted to the implant fixture with these anti-rotation devices engaged one in the other, prior to turning the screw 12 into the bore 18.

Figures 3, 4:
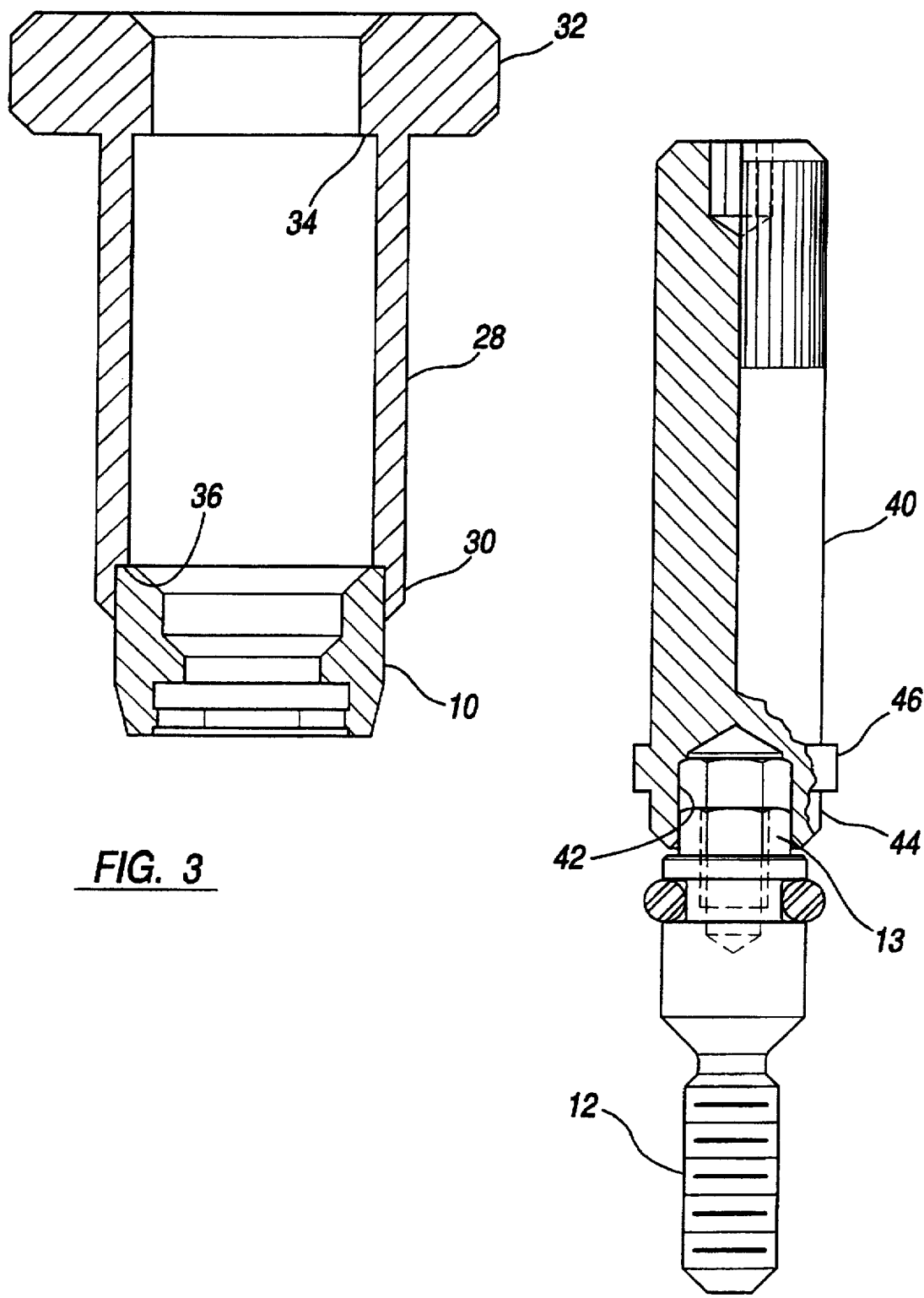
FIG. 3 illustrates a tubular part for holding the transmucosal component.
FIG. 4 illustrates a part for holding the screw.

FIG. 3 shows in longitudinal section a tubular holder part 28 for the transmucosal component 10. The internal diameter of this holder part is expanded at its lower end 30 to provide a recess with an internal shoulder 36 for receiving the supragingival end of the transmucosal component. The wall around the recess can be longitudinally slotted if desired to provide a circular array of resilient fingers (see FIG. 6) for releasibly holding the transmucosal component; alternatively the holder part 28 can be made of a resilient plastic material, in which case the wall around the recess can be continuous and the normal resilience of the plastic material will suffice to do the same thing. At its other end the holder has an expanded head 32 gripping it and a second internal shoulder 34 for a purpose to be described.

The second holder part 40 shown in FIG. 4 is cylindrical in shape for telescopically fitting within the tubular holder part 28. This second part has a socket 42 in its lower end 44 for embracing the head 13 of the screw 12. This particular screw has a hexagonally-shaped head, and the socket 42 in the illustrated embodiment is matingly hexagonal. This is an optional feature adopted to accommodate a particular screw; the invention is not limited to it. For example, the male-female relation of the head 13 and the socket 42 may be reversed. An annular boss 46 is also located near the lower end 44. When, as is illustrated in FIG. 5, the second holder part 40 is telescopically fitted within the tubular holder part 28 the boss 46 will stop against the second shoulder 34.

Figure 5:
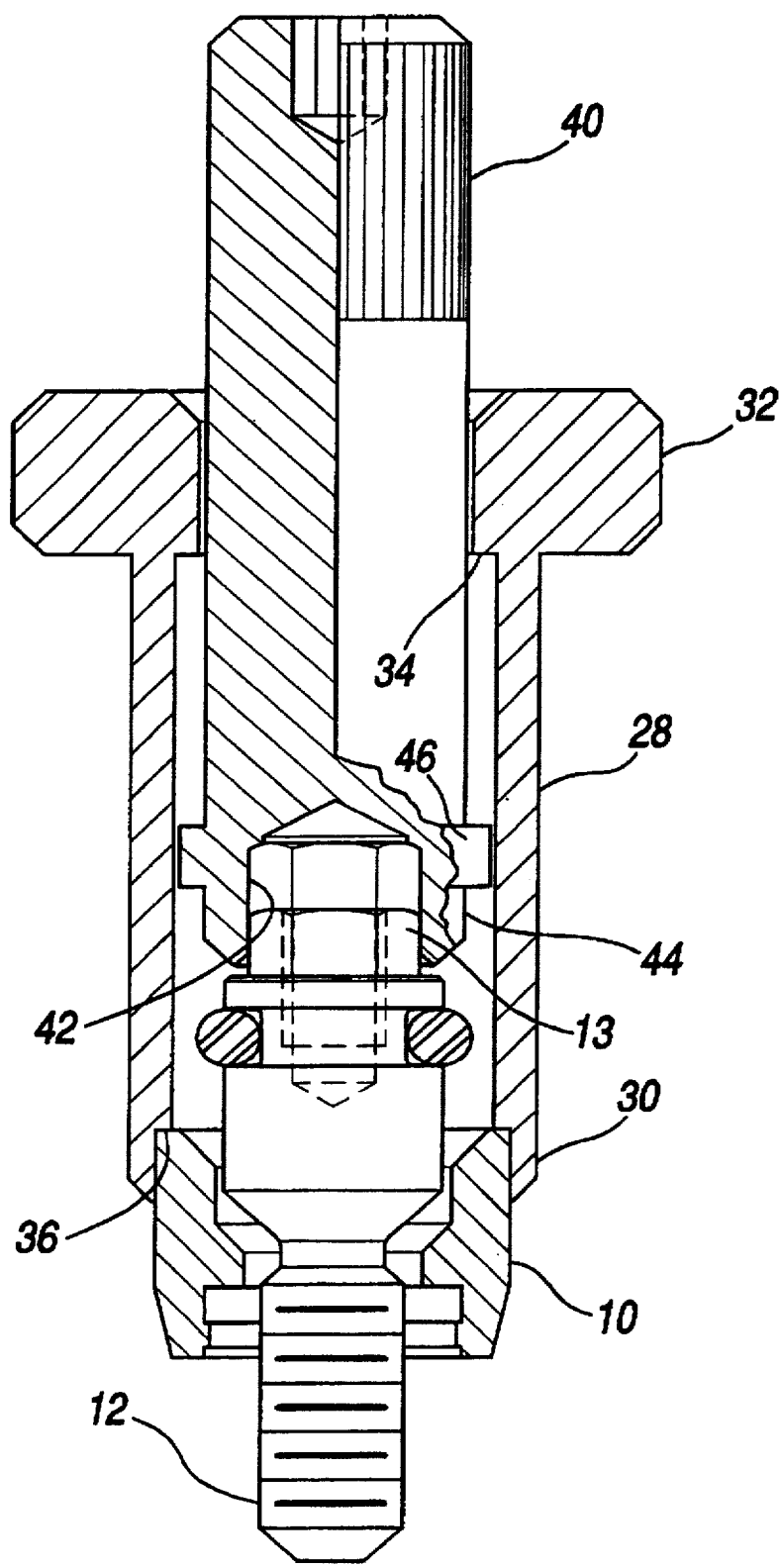
FIG. 5 shows the parts of FIGS. 3 and 4 telescopically interfitted and holding the transmucosal component and the screw in the relative positions they will occupy for installation on the implant fixture.

Referring now to FIG. 5, the two holder parts are shown with the second part 40 telescopically interfitted in the tubular part 28. To do this, the second part with the screw 12 engaged may be inserted through the lower end 30 of the tubular part 28, and thereafter the transmucosal component 10 may be attached to the tubular part. This arrangement provides an assembly of the holder-carrier 28, 40 and the dental components 10, 12 which can be brought as a unit to the dental implant fixture 14 with two fingers (e.g.: thumb and forefinger) of one hand holding the assembly by the expanded head 32. At the implant fixture, the transmucosal component is then manipulated into place on the implant fixture and, while gently holding the transmucosal component against the implant fixture, the second holder part is turned to drive the screw 12 into the threaded bore 18. This assembly can be delivered as a unit to the end user, i.e.: a prosthodontist, periodontist, oral surgeon or other qualified dental professional. It lends itself to encapsulation in a sterile package, if desired.

Figure 5A:
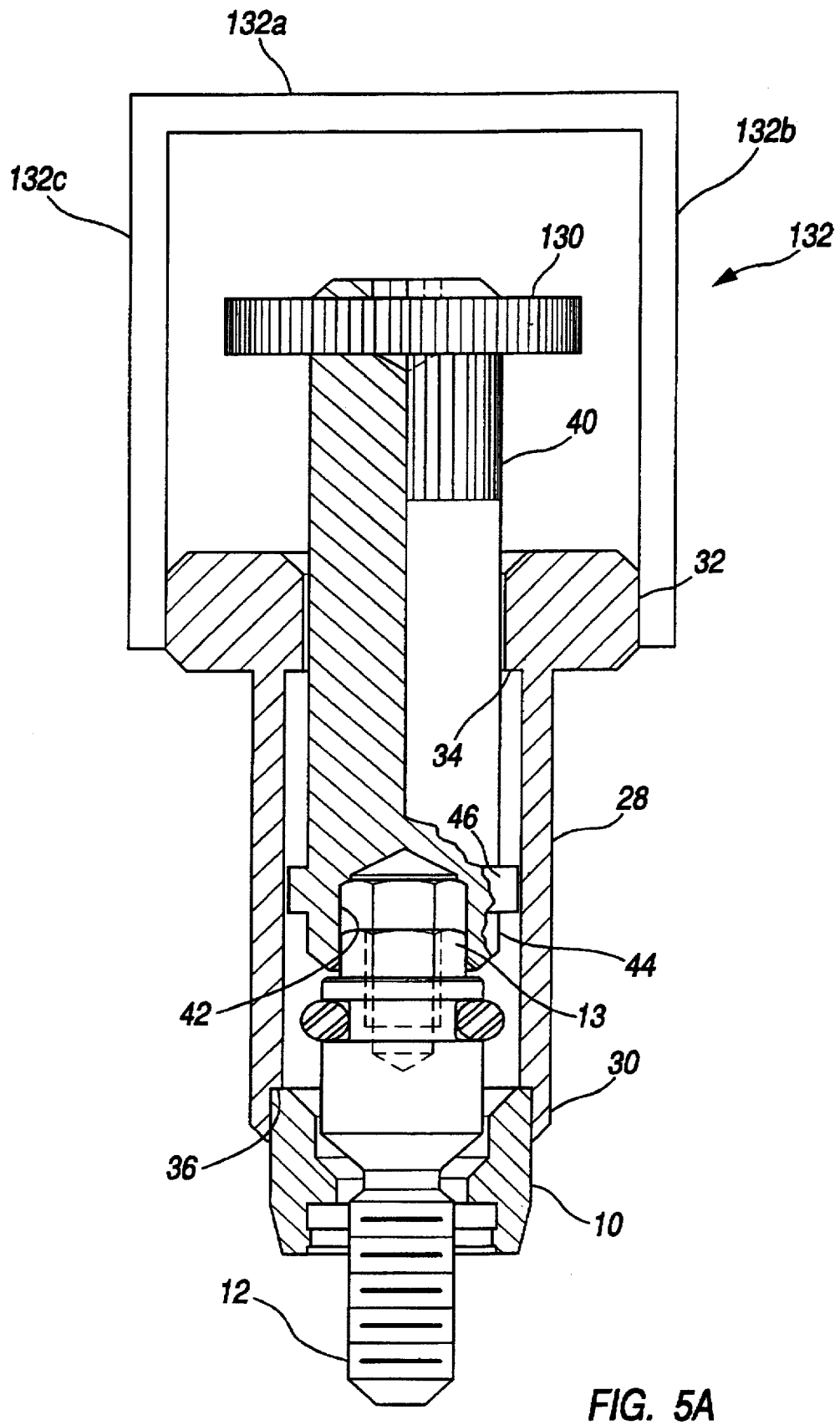
FIG. 5A is a modification of FIG. 5.

In FIG. 5A a manipulator 130 is fixed to the upper end of the second (driver) part 40, and holder means 132 having a bight portion 132a and two substantially parallel arms 132b and 132c is attached at the free ends of the arms to substantially diametrically opposite sides of the head 32 of the holder part 28. The bight portion 3132a overlies the manipulator 130, and the manipulator fits between the arms 132b and 132c. In use, the holder means carries the assembled tool with the screw 12 and component 10 to a work site, where the bight portion 132a can be used to press the component to the implant with one finger while the manipulator can be turned with two other fingers of the same hand.

Figure 6:
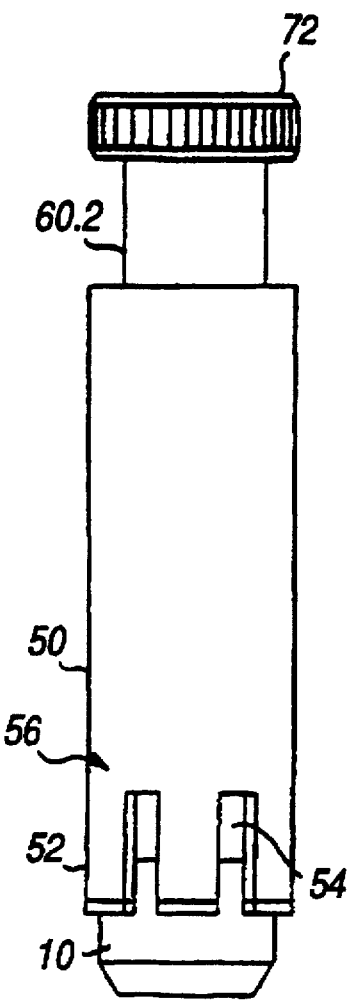
FIG. 6 is a side view of another embodiment of the invention.
Figure 7:
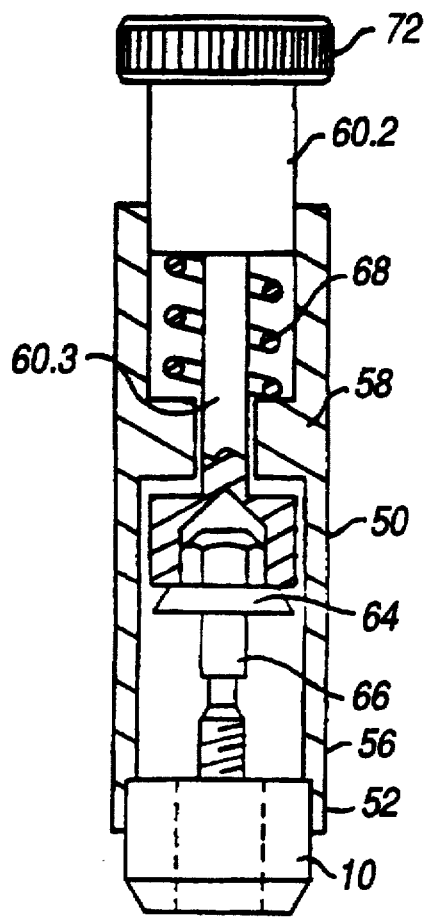
FIG. 7 is a longitudinal section through FIG. 6 showing a spring used to aid in a two-finger installation.

The embodiment of the invention that is illustrated in FIGS. 6, 7 and 8 is unitary tool which includes a means to hold down the tubular part of the invention while turning the screw component with the second part of the invention. This embodiment is also designed to be compact so that it will minimally obscure the user's view of the task being performed, and will be easy and economical to package and ship. The outer tubular part 50 has spring-fingers 52 separated by longitudinal slots 54 at its lower end 56 for holding the abutment 10. The inner second part 60 is an assembly of two members, a head member 60.2 and a screw-holder member 60.1 having a stem 60.3. The tubular part 50 has a diametrically reduced section 58 between its ends providing a first shoulder 58.1 facing the lower end 56 and a second shoulder 58.2 facing in the opposite direction. The holder member 60.1 has a socket member 60.4 of larger diameter than its stem 60.3 affixed to the lower end of the stem, and forming a shoulder 60.5 where it joins the stem. The socket member has a non-round socket 62 for holding the matingly non-round head 64 of a screw 66 which is equivalent to the screw 12. To assemble this tool the stem 60.3 is passed through the lower end 56 of the tubular part 50 and through the reduced section 58 so that the shoulders 58.1 and 60.5 confront each other, a coil spring 68 is fitted over the stem 60.3 in the upper well 70 of the tubular part, and the head member 60.2 is press-fitted onto the free end of the stem. A turning knob 72 is provided on the free end of the head member.

In use, the screw 66 is fitted into the socket 62 and the component 10 is thereafter fitted into the spring fingers 52. This assembly is then carried to the installed implant fixture and the abutment is put in place on the implant fixture with the outer part 50. The knob 72 may then be grasped between the thumb and forefinger and pressed down toward the implant while the knob is turned to drive the screw into the implant fixture. The spring 68 provides resilient force to hold the component 10 on the implant while the screw is being turned.

The tool of FIGS. 6, 7 and 8 may be made of materials such as stainless steel which can be autoclaved. No lubricant is used in its construction. Alternatively this tool can be made of disposable materials and it can be delivered to the user in a sterile package including the component and screw to be installed on an implant fixture.

FIG. 9 shows the tool of FIG. 6 enclosed in a capsule 80, which may be made of glass or plastic, for example, and is closed with a cap 82 which may be made of rubber or plastic, for example. The outer tubular part 50 is located with an O-ring 84 within the capsule. As is shown, the abutment 10 may be held against the bottom of the capsule, to prevent it from falling away from the spring fingers 52. In use, the cap 82 is removed and the tool is removed from the capsule with the turning knob 72 which is then used to carry the abutment 10 and screw 66 directly to the dentalimplant fixture 14.

Figure 10:
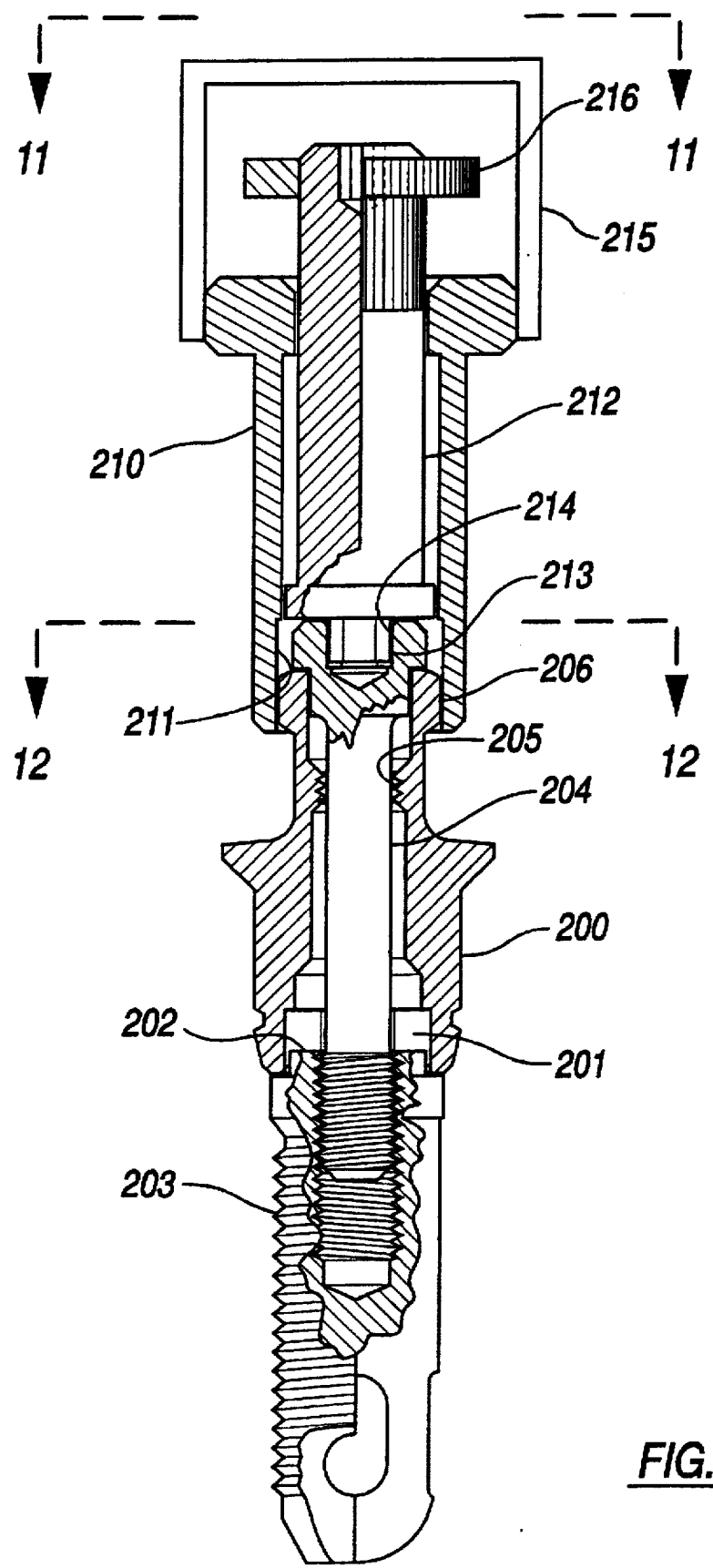
FIG. 10 is a longitudinal section through a modified embodiment of the invention for use in handling and manipulating an implant carrier and its attachment screw.
Figure 11:
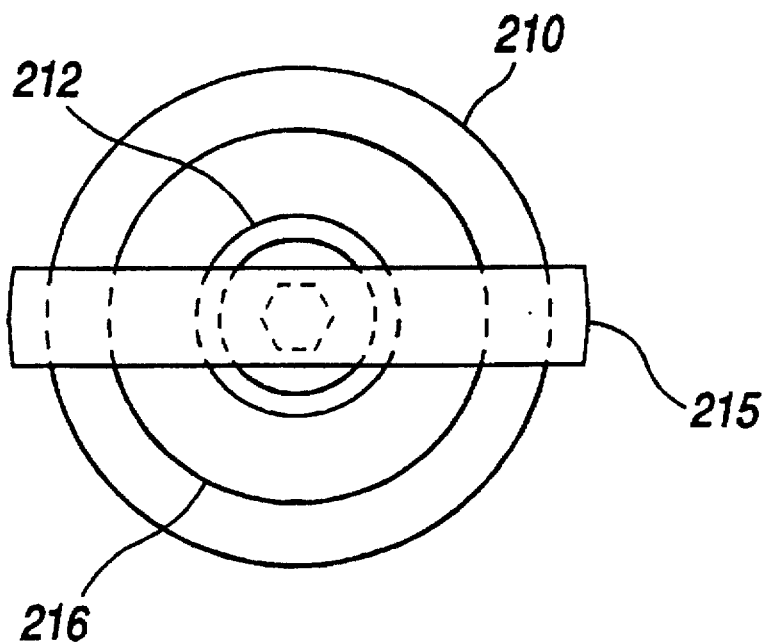
FIG. 11 is an end view taken from the top end of the assembly shown in FIG. 10.
Figure 12:
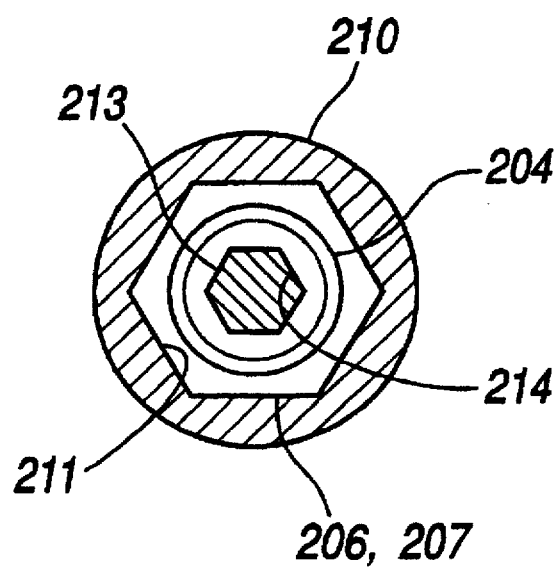
FIG. 12 is a section taken generally along line 12—12 in FIG. 10.

A modified embodiment of the invention, for use in handling and manipulating a dental implant carrier, is illustrated in FIGS. 10-12. An implant carrier is a device that is used to hold an implant as it is inserted into a patient's mouth and installed into a prepared site in the patient's jawbone. The carrier is also used to turn the implant to thread it into the jawbone.

In FIG. 10, an implant carrier 200 has a hexagonal socket 201 formed in its lower end for receiving a complementary hexagonal head 202 on the top of a dental implant 203. The implant 203 is held securely on the carrier 200 by a screw 204 which extends longitudinally through the hollow interior of the carrier 200 and is threaded into an internally threaded bore in the top of the implant. To prevent the screw 204 from escaping from the carrier 200, the screw 204 must be threaded through a short internally threaded section 205 of the carrier before the screw can be threaded into the implant. Thus the screw is captured within the carrier 200.

To permit the implant 203 to be threaded into the jawbone of the patient by turning the carrier 200, which will still extend well above the gingiva even when the implant is in its desired final position within the jawbone, the carrier has a hexagonal head 206 that can be engaged by a standard wrench or other suitable driver. Turning the carrier 200 causes turning of the implant 203. After the implant has been threaded into the patient's jawbone, the screw 204 is threaded out of the implant to permit the carrier and its captive screw to be removed from the implant and the patient's mouth.

For the purpose of facilitating the handling and placement of the carrier-implant assembly, a holder 210 has a hexagonal socket 211 in its lower end for receiving and frictionally retaining the hexagonal head 206 of the carrier 200. Captured within the holder 210 is a driver 212 having a small hexagonal head 213 on its lower end, for engagement with a complementary haxagonal socket 214 in the top of the carrier screw 204. If desired, the driver may be designed as described in U.S. Pat. No. 5,105,690, which is incorporated herein by reference. The driver 212 can be rotated within the holder 210 for threading the screw 204 in and out of the implant 203, which is particularly useful for removal of the screw from the implant after the implant is in place in the patient's mouth.

As in the case of the bolder described above in connection with FIG. 5a, the holder 210 has a handle or manipulator 215 extending upwardly from, and diametrically across, the top of the holder. This handle 215 extends across the top of the driver 212, which is equipped with a knurled knob 216 which extends laterally beyond opposite sides of the handle 215 (see FIG. 11). Consequently, both the handle 215 and the knob 216 can be simultaneously gripped and manipulated with the thumb and forefinger of the person installing the implant in the patient. This is a significant advantage when working within the close confines of a patient's mouth.

If desired, the holder 210 can also be used as the driving tool for turning the implant carrier 200, and thus the implant itself, to thread the implant into the patient's jawbone. Here again, the handle 215 on the top of the holder 210 can be used to advantage.

We claim:

1. A tool for use in manually inserting a dental implant into a prepared implant site in a bone in the mouth of a patient, said tool comprising an implant carrier having a lower end for engaging the top of the dental implant so that the implant can be rotated by rotating the carrier, a screw passing longitudinally through the implant carrier and threaded into the top of the dental implant for holding the implant on the implant carrier, a holder for the implant carrier, said holder having a lower end for engaging the top of the implant carrier so that the implant carrier is retained in the holder, a driver mounted for rotation in said holder and extending downwardly through said holder for engaging the top of said screw, so that said screw can be rotated by rotating the driver, the top of said driver extending above the top of said holder so that said driver can be turned with the fingers of the person installing the implant, and a handle attached to the top of said holder and extending upwardly from said holder to permit the person installing the implant to simultaneously manipulate said holder and turn said driver with fingers of the same hand.

2. The tool of claim 1 wherein mating male and female anti-rotation elements are formed on the top of said implant and the bottom of said implant carrier.

3. The tool of claim 1 wherein the bottom of said holder forms a socket for receiving the top of said implant carrier.

4. The tool of claim 1 wherein said handle is formed as an integral part of said holder.

5. The tool of claim 1 wherein said handle extends over the top of said driver.

6. The tool of claim 1 wherein the top of said driver forms an enlarged head which extends laterally beyond said handle to facilitate turning of said driver with the same fingers that grip said handle.

7. The tool of claim 1 wherein mating male and female anti-rotation elements are formed on the top of said screw and the bottom of said driver.

8. A tool for use in manually positioning and manipulating a selected article at a prepared implant site in a bone in the mouth of a patient, said tool comprising an article holder having a lower end for engaging the top of the selected article, a fastener passing longitudinally through said article holder for cooperation with the selected article engaged by the lower end of said article holder, a driver mounted for rotation in said article holder and extending downwardly through said article holder for engaging the top of said fastener, so that said fastener can be rotated by rotating the driver, the top of said driver extending above the top of said article holder so that said driver can be turned with the fingers of the person positioning and manipulating the selected article, and a handle attached to the top of said article holder and extending upwardly from said article holder to permit the person positioning and manipulating the selected article to simultaneously position and manipulate said holder and turn said driver with fingers of the same hand.

9. The tool of claim 8 wherein said selected article is an implant carrier, and said fastener is a screw for attaching an implant to said implant carrier.

10. The tool of claim 8 wherein said selected article is an implant abutment, and said fastener is a screw for attaching said abutment to an implant.

11. The tool of claim 8 wherein said driver has a knob on its upper end to facilitate turning said driver, and said handle extends across the top of said knob to facilitate manipulation of said article holder with the same fingers used to turn said driver.

12. A tool for use in manually inserting a dental implant into a prepared implant site in a bone in the mouth of a patient, said tool comprising an implant carrier having a lower end for engaging the top of the dental implant so that the implant can be rotated by rotating the carrier, a screw passing longitudinally through the implant carrier and threaded into the top of the dental implant for holding the implant on the implant carrier, a holder for the implant carrier, said holder having a lower end for engaging the top of the implant carrier so that the implant carrier is retained in the holder, a driver mounted for rotation in said holder and extending downwardly through said holder for engaging the top of said screw, so that said screw can be rotated by rotating the driver, the top of said driver extending above the top of said holder so that said driver can be turned with the fingers of the person installing the implant, and a manipulating and turning means attached to said holder to permit the person installing the implant to simultaneously manipulate said holder and turn said driver with fingers of the same hand.

13. A tool for use in manually positioning and manipulating a selected article at a prepared implant site in a bone in the mouth of a patent, said tool comprising an article holder having a lower end for engaging the top of the selected article, a fastener passing longitudinally through said article holder for cooperation with the selected article engaged by the lower end of said article holder, a driver mounted for rotation in said article holder and extending downwardly through said article holder for engaging the top of said fastener, so that said fastener can be rotated by rotating the driver, the top of said driver extending above the top of said article holder so that said driver can be turned with the fingers of the person positioning and manipulating the selected article, and a positioning and manipulating means attached to said article holder to permit the person positioning and manipulating the selected article to simultaneously position and manipulate said holder and turn said driver with fingers of the same hand.

* * * * *